(12) United States Patent
Kitazawa et al.

(10) Patent No.: US 7,627,379 B2
(45) Date of Patent: Dec. 1, 2009

(54) METHOD OF SPEECH CONVERSION IN A COCHLEAR IMPLANT

(75) Inventors: Shigeyoshi Kitazawa, Shizuoka-ken (JP); Shinya Kiriyama, Shizuoka-ken (JP); Erdenebat Dashtseren, Shizuoka-ken (JP); Satoshi Iwasaki, Shizuoka-ken (JP)

(73) Assignee: Hamamatsu Foundation for Science and Technology Promotion, Shizuoka-ken (JP)

( * ) Notice: Subject to any disclaimer, the term of this patent is extended or adjusted under 35 U.S.C. 154(b) by 474 days.

(21) Appl. No.: 11/349,423

(22) Filed: Feb. 7, 2006

(65) Prior Publication Data
US 2006/0217784 A1   Sep. 28, 2006

Related U.S. Application Data

(63) Continuation of application No. PCT/JP2004/011077, filed on Aug. 3, 2004.

(30) Foreign Application Priority Data
Aug. 7, 2003   (JP)   ............... 2003-206405

(51) Int. Cl.
*A61N 1/00* (2006.01)
(52) U.S. Cl. ...................................................... 607/57
(58) Field of Classification Search ............... 607/55, 607/56, 57, 136, 137; 381/45, 59; 379/406.08; 367/129; 375/340, 316, 142; 347/247
See application file for complete search history.

(56) References Cited

U.S. PATENT DOCUMENTS
4,390,756 A * 6/1983 Hoffmann et al. ............ 607/56
(Continued)

FOREIGN PATENT DOCUMENTS
WO   WO 2001/013991 A1   3/2001
(Continued)

OTHER PUBLICATIONS
International Search Report of PCT Application No. PCT/JP2004/011077, issued on Nov. 2, 2004.
(Continued)

*Primary Examiner*—George Manuel
*Assistant Examiner*—Robert N Wieland
(74) *Attorney, Agent, or Firm*—Knobbe Martens Olson & Bear LLP (57) ABSTRACT

A method for speech conversion in an artificial auris interna and an artificial auris interna can be capable of providing speech near to natural speech to a person using the artificial auris interna and reproducing natural fluctuation at random with a value near to the periodicity unique to each channel. Within a signal frame, speech information can be distinguished according to each frequency band by using band pass filters. Channel information on the corresponding frequency band can be added to the speech information. For each channel, speech information having a large signal level within one channel is left so that the number of stimulus pulses can be adjusted to be a frequency allowed for one channel. From all the speech information left for each channel, the speech information having a large signal level is left so that the number of stimulus pulses is adjusted to be a frequency allowed for the entire channel. The remaining speech information is transmitted to an electrode corresponding to the channel, thereby generating a stimulus pulse.

7 Claims, 9 Drawing Sheets

U.S. PATENT DOCUMENTS

| | | | | |
|---|---|---|---|---|
| 4,593,696 A | * | 6/1986 | Hochmair et al. | 607/57 |
| 5,870,436 A | * | 2/1999 | Kolanek et al. | 375/316 |
| 2003/0014088 A1 | * | 1/2003 | Fang et al. | 607/48 |

FOREIGN PATENT DOCUMENTS

| WO | WO 2001/056521 A1 | 8/2001 |
|---|---|---|

OTHER PUBLICATIONS

Supplementary European Search Report of EP Application No. 04748210, issued on Jun. 27, 2007.

Philipos L Loizou, "Mimicking the human ear: An Overview of Signal-Processing Strategies for Converting Sound into Electrical Signals in Cochlear Implants", IEEE Signal Processing Magazine, Sep. 1998, pp. 101-130, XP011089814.

* cited by examiner

METHOD OF SPEECH CONVERSION IN A COCHLEAR IMPLANT

RELATED APPLICATIONS

This application is a Continuation of PCT Application No. PCT/JP2004/011077, filed Aug. 3, 2004, which claims priority to Japanese Application No. 2003-206405, filed Aug. 7, 2003, the entire contents of both of which are hereby incorporated by reference.

BACKGROUND OF THE INVENTIONS

1. Field of the Inventions

The present inventions relate to methods of speech conversion, for example, for use with cochlear implants (artificial cochlear) in which acoustic information is provided to the cochlea in the form of electrical stimulation.

2. Description of the Related Art

Heretofore, cochlear implants have been provided with an electrode having an array of electrodes arranged within the cochlea. These implants discriminate speech from other sounds by sampling sound with a microphone, and dividing the sound into respective frequency bands with a plurality of band pass filters. Some or all of these frequency bands can carry speech.

The sounds from the respective frequency bands, which can include speech, are transmitted to the electrodes corresponding to channels, to thereby generate electrical stimulation pulses. As such, speech and/or other sounds can be transmitted to the cochlea as electrical stimulation pulses.

The speech conversion is carried out by converting the speech information to the stimulation pulses using a speech processor arranged within the cochlear implant. In such a cochlear implant, it is impossible to obtain a faithful sound reproduction relative to actually processed speech signals when the electrodes are simultaneously stimulated. This is because of generation of unsuitable stimulation caused by mutual action between electrode circuits when the electrodes are simultaneously stimulated.

For resolving such a problem, a continuous interleaved sampler (CIS) system has been adopted as the conventional speech converting method in the cochlear implant. In this system, all channels are successively stimulated at a predetermined interval in order to avoid the simultaneous stimulation of channels and thus all speech information is transmitted without any omission. That is, no speech information can be output until it arrives at its order although it is generated simultaneously with other speech information.

Since the CIS is not a known invention disclosed in any publication, there is no information relating to publications of the prior art.

According to the CIS system of the prior art, since all channels are successively stimulated at a predetermined interval, speech can sometimes be output at a timing delayed from that at which the speech is actually generated and thus the regenerated speech can sound unnatural to the patient.

SUMMARY OF THE INVENTIONS

It is, therefore, an object of at least one of the present inventions to provide a cochlear implant and a method of speech conversion in the cochlear implant which can provide a user with speech reproduction of a more natural feeling and can regenerate a natural variation at a value near the natural period of respective channels.

Thus, in accordance with an embodiment, a method of speech conversion in a cochlear implant can be provided. The method can include discriminating the sound information into respective frequency bands using a plurality of band pass filters within a signal frame of a predetermined sampling period and adding an information indicative of a channel corresponding to the frequency band to the sound information. The method can also include adjusting the number of the stimulation pulses to a frequency in one channel by leaving, in respective channels, a sound information having a higher signal level in one channel and adjusting the number of the stimulation pulses to a frequency in all channels by leaving a sound information having a higher signal level in all sound information left in the respective channels. Finally, the method can include generating the stimulation pulses by providing the remaining sound information to the electrode corresponding to the channel.

In accordance with another embodiment, a cochlear implant can be provided. The implant can include a channel information adding means for adding an information of a channel corresponding to the frequency band to the sound information after discriminating the sound information into respective frequency bands using a plurality of band pass filters within a signal frame of a predetermined sampling period. The implant can also include an in-channel stimulation frequency adjusting means for adjusting the number of the stimulation pulses to a frequency allowed in one channel by leaving in respective channels within the signal frame a sound information having a higher signal level in one channel and an inter-channel stimulation frequency adjusting means for adjusting the number of the stimulation pulses to a frequency allowed in all channels by leaving a sound information having a higher signal level in all sound information left in respective channels. Additionally, the implant can also include a stimulation pulse generating means for converting the remaining sound information to the stimulation pulse and providing the stimulation pulse to the electrode corresponding to the channel.

In yet another embodiment, a cochlear implant can be provided. The implant can include a channel information adding module configured to correlate the sound information into respective frequency bands using a plurality of band pass filters within a signal frame of a predetermined sampling period and to add an information of a channel corresponding to the frequency band to the sound information. The implant can also include an in-channel stimulation frequency adjusting module configured to limit the number of the stimulation pulses to a frequency allowed in one channel by leaving in the respective channels within the signal frame a sound information having a higher signal level in one channel and an inter-channel stimulation frequency adjusting module configured to limit the number of the stimulation pulses to a frequency allowed in all the channels by leaving a sound information having a higher signal level in all sound information remaining in the respective channels. Additionally, the implant can include a stimulation pulse generating module configured to convert the remaining sound information into stimulation pulses and providing the stimulation pulses to the electrode corresponding to the channel.

BRIEF DESCRIPTION OF THE DRAWINGS

These and other features, aspects and advantages of the present inventions are better understood with reference to preferred embodiments, which are illustrated in the accompanying drawings. The illustrated embodiments are merely exemplary and are not intended to define the outer limits of the scope of the present inventions. The drawings of the illustrated arrangements comprise the following figures.

DETAILED DESCRIPTION OF THE PREFERRED EMBODIMENT

Embodiments including methods and systems for sound conversion are described with reference to accompanying drawings. The methods and systems disclosed herein are described in the context of cochlear implants because these methods and systems have particular utility in this context. However, the embodiments of the methods and systems described below can also be used in other contexts as well. For example, the methods and systems of sound conversion described hearing can also be used in other types of sound conversion equipment.

Additionally, it is to be noted that although the term "speech" is used in the following description, it should be noted that "speech" is intended to include not only a voice of human but any other audible sounds.

Figure 1:
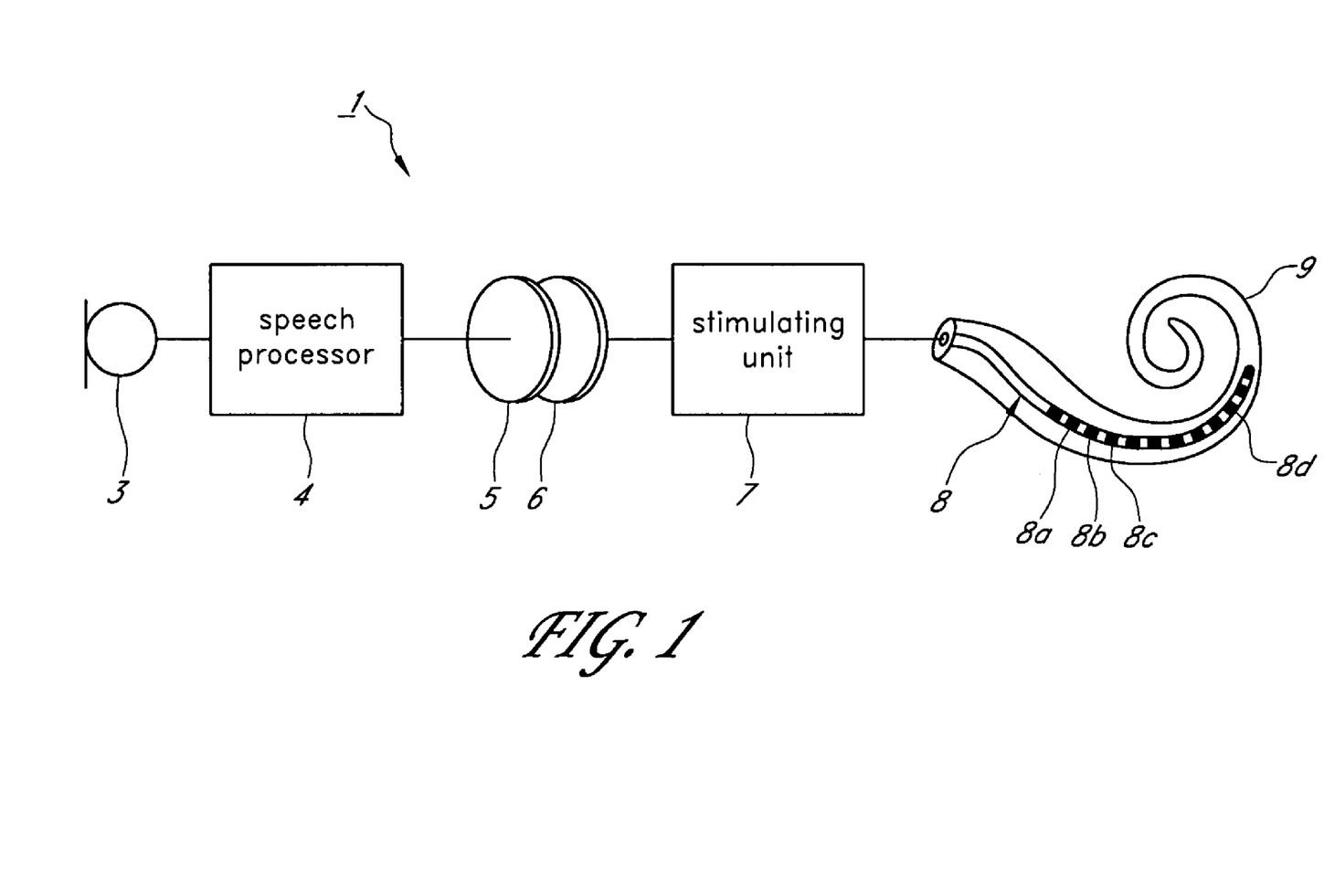
FIG. 1 is a block diagram schematically showing the structure of the cochlear implant according to an embodiment.

A cochlear implant 1 can be adapted to enhance the acoustic sense of the patient by providing electrical stimulation pulses to the cochlea 9. For example, the cochlear implant 1 can comprise a microphone 3, a sound processor 4 figured to perform the sound conversion process of converting sound information sampled via the microphone 3 into stimulation pulses. The cochlear implant 1 can also include an external coil 5 forming an antenna outside of the human body of the patient, an internal coil 6 forming an antenna within the human body of the patient, a stimulating unit 7 for converting the sound information sent from the speech processor 4 via the external and internal coils 5 and 6 into the stimulation pulses, and an electrode array 8 consisting of a plurality of electrodes 8a~8d arranged within a cochlea for output of the stimulation pulses into the cochlea 9. The sound, which is in the form of electronic stimulation pulses, can be sensed by the human acoustic nerve with its end being stimulated by an electric current generated by the electrodes 8a~8d.

The electrodes 8a~8d of the electrode array 8 can include, in some nonlimiting embodiments, about 22 electrodes, each being adapted to be used based on the condition of a user. The audible speech or sound range can be divided into M bands, each forming a channel, with each of the electrodes 8a~8d corresponding to one of the channels. Although the illustrated embodiment can be described based on an example using 4 (four) electrodes 8a~8d, the present embodiments and inventions are not limited to the illustrated embodiment.

Accordingly, in some embodiments, the electrode 8a can be a 21-th electrode (channel (Ch.) 21) having its center frequency of about 6226 Hz, the electrode 8b can be a 20-th electrode (channel (Ch.) 20) having its center frequency of about 5314 Hz, the electrode 8c can be a 19-th electrode (channel (Ch.) 19) having its center frequency of about 907.1 Hz, and the electrode 8d can be a 3-rd electrode (channel (Ch.) 3) having its center frequency of about 466.5 Hz. However, other numbers of channels and other center frequencies can also be used.

The operation of the cochlear implant 1 according to the present embodiment is described below. In the description set forth below, bracketed reference numerals such as "(S101)", "(S102)" . . . , correspond to those shown in flow charts of FIG. 2~FIG. 5.

Figure 2:
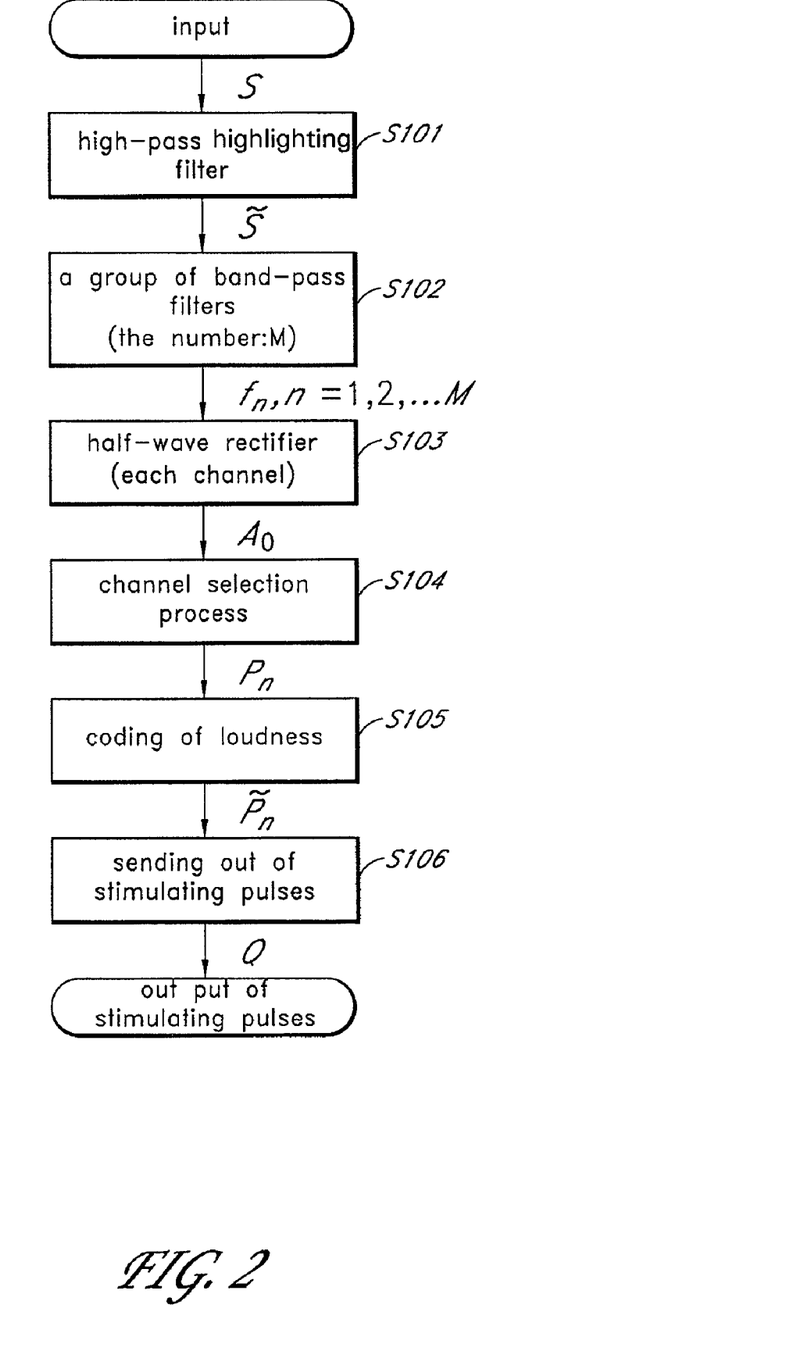
FIG. 2 is a flow chart showing an operation of the cochlear implant according to an embodiment.

Initially, an overall operation of the cochlear implant 1 is described. During operation, a signal S can be picked up by the microphone 3 and can then be reshaped by a high-pass highlighting filter (S101). The reshaped signal can then be passed through one or more band-pass filters (S102).

With a plurality of band-pass filters, the signal S can be discriminated into respective frequency bands. In some embodiments, the signal S can be discriminated into M frequency bands.

In some embodiments, the information indicative of the channel of the corresponding frequency band can be added to the sound information. That is, for example, the group of band-pass filters can include one or more channel information adding modules configured to add indicia or data indicating the channel or frequency band from which the sound information came.

And some embodiments, the signal S can then be regulated to a desired data style by half-wave rectifiers of the respective channels (S103). For example, sound information can be combined with channel information, time information and signal level information. For example, but without limitation, such information can be converted into an amplitude-time matrix (ATM). This can be expressed as a following mathematical expression (1) in which I and M are numbers of channel, and T and N are time information in which their sound information appear.

$$A_0 = \begin{bmatrix} a_{1,1} & a_{1,2} & \cdots & a_{1,N} \\ a_{2,1} & a_{2,2} & \cdots & a_{2,N} \\ \vdots & \vdots & \vdots & \vdots \\ a_{M,1} & a_{M,2} & \cdots & a_{M,N} \end{bmatrix} \quad (1)$$

$$I = \{1, 2, 3, \ldots, M\}$$

$$T = \{1, 2, 3, \ldots, N\}$$

The sound information written as the ATM can be within a signal "frame" of sound. Such a "frame" can be defined as a predetermined and fixed sampling period. However, the sampling period used to define a "frame" can be of varying periods that are changed in accordance with a predetermined schedule, or can be dynamically changed during operation in accordance with other considerations. Following processes can be successively repeated in respective signal frames.

The length of the signal frame in the some embodiments, for example, but without limitation, can be about 10 mS, however the signal frame length is not limited to 10 mS. The length of the signal frame can be determined in consideration of facts that the regeneration of the sound information can be delayed if the length of the signal frame can be too long. On the other hand, the sound information might not be reliably detected if it is shorter than the fundamental period of the specific sound such as human speech (a period of vibration of the vocal cord).

Then a channel selection process for the speech extraction process can be used for the actually output stimulation pulses from the speech information of the ATM (S104). The detail of the channel selection process is described below in more detail. After the channel selection process, the signal level (including the electric current level) can be adjusted so that the speech information obtained by the channel selection process can be converted into stimulation pulses that can provide a suitable sound feeling (loudness) in accordance with the dynamic range of the stimulation pulses (S105). The obtained speech information can be sent to the stimulating unit 7 and the stimulating pulses can then be output from each of the electrodes 8a~8d (S106).

Figure 3:
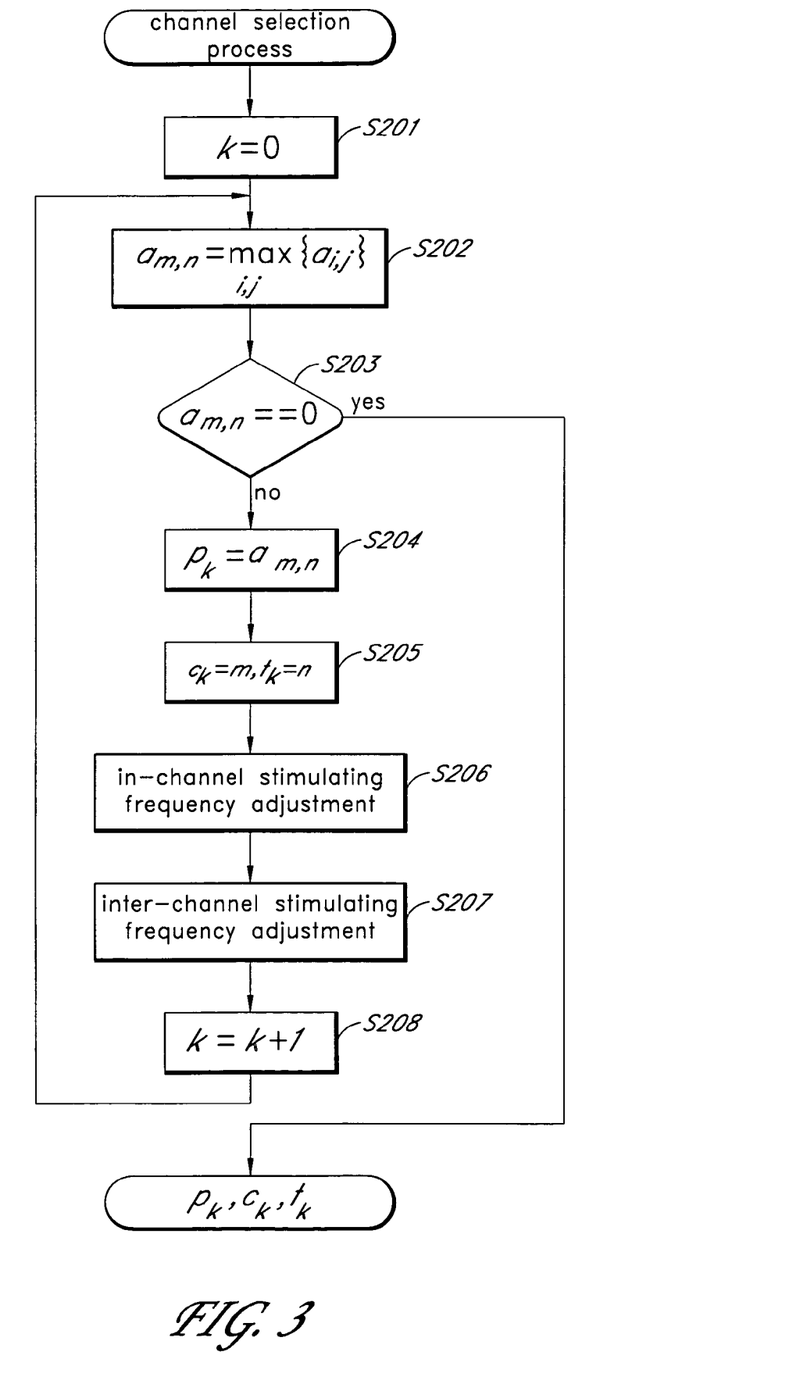
FIG. 3 is a flow chart showing an operation of a channel selection process of the cochlear implant according to an embodiment.

Next, the channel selection process (S104) is described with reference to FIG. 3. Firstly, a counter "k" in the channel selection process can be reset (S201). Then the speech information in the ATM can then be put in order of magnitude of the signal level (S202). At this point of time, if the maximum value is zero (0), no more process is required and thus the process can be completed (S203: yes).

The highest signal level of the sound information, the information indicative of channel, and the information indicative of the time are correlated with variables $p_k$, $c_k$, and $t_k$ respectively, (S204 and S205). A mathematical expression (2) for determining the maximum value $p_k$ can be shown as follows:

$$a_{m,n} = \max_{i,j}\{a_{i,j}\}, \ p_k = a_{m,n}, \ i \in I, \ j \in T \quad (2)$$

After S205, an in-channel stimulating frequency adjustment can be carried out for adjusting the number of the stimulation pulses to a frequency (stimulating rate) allowed in one channel by leaving in respective channels within the signal frame a speech information having a highest signal level within the respective channel (S206).

Figure 7:
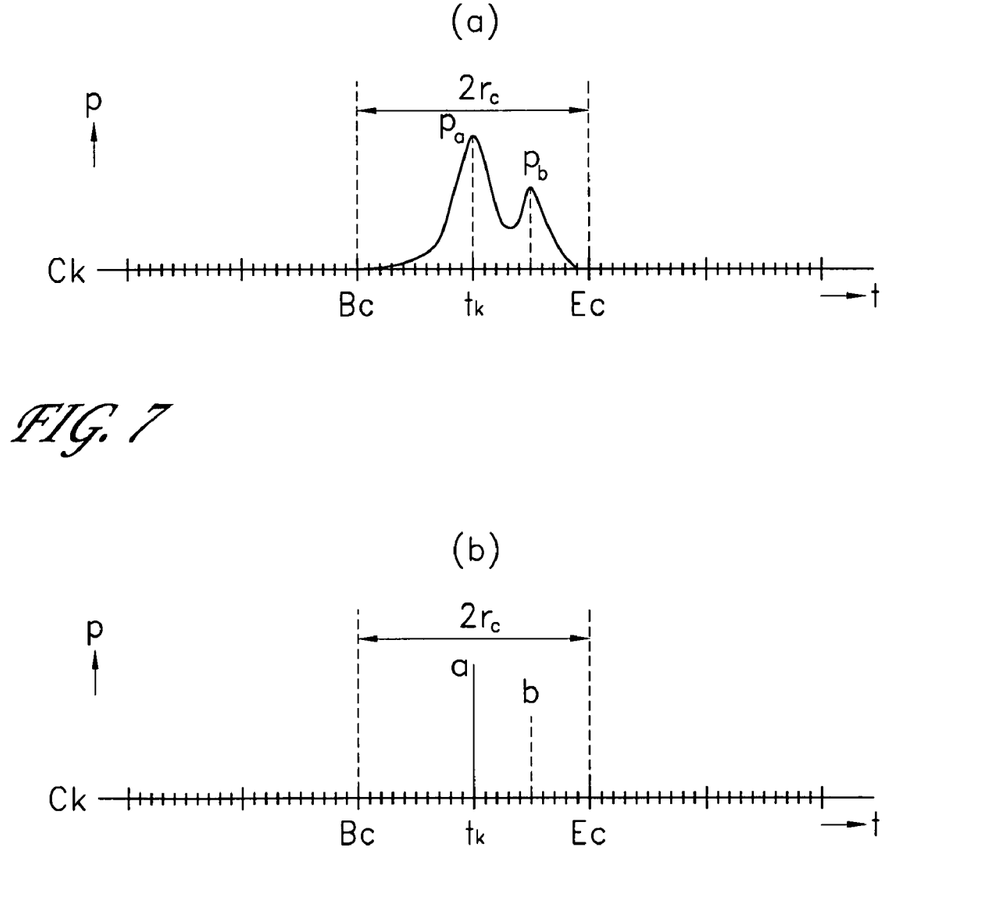
FIG. 7 includes timing diagrams showing the operation of the in-channel stimulating frequency adjusting module of the cochlear implant according to an embodiment.

The in-channel stimulating frequency adjustment is described with reference to FIG. 7. FIG. 7 (a) is a graph having the abscissa (time: t) and the ordinate (signal level: p) and shows a speech information before process of the channel k(ck). The scale of the abscissa indicates the sampling rate. That is, the scale unit of the abscissa indicates the presence of the speech information before treatment. The sampling rate can be for example, but without limitation, 20 kHz. A symbol "rc" is the inverse number of the channel stimulating rate Rc (e.g. 1800 pps) and indicates a period in which the presence of only one stimulation pulse is allowed. The channel stimulating rate Rc can be a stimulating rate per one channel.

Figure 4:
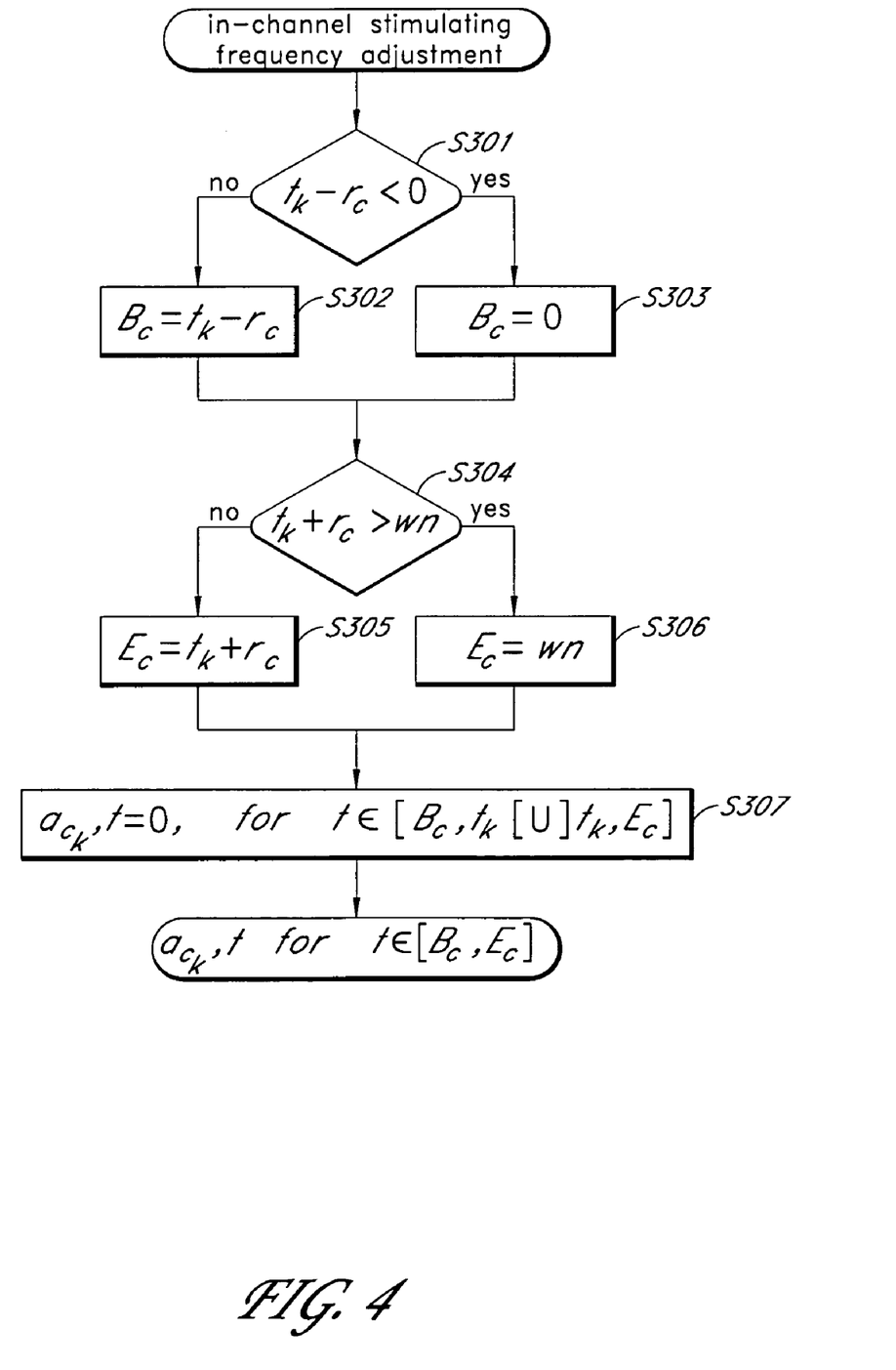
FIG. 4 is a flow chart showing an operation of the in-channel stimulating frequency adjusting module of the cochlear implant according to an embodiment.

In one time in-channel stimulating frequency adjustment, it should be processed during a period from a point of time (Bc) before from a point of time tk by a period rc, to a point of time (Ec) after from a point of time tk by a period rc. Bc can be determined as a time which can be obtained by subtracting rc from tk (S302), if the value obtained by subtracting rc from tk can be larger than zero (0) (S301: no) and can be also determined as zero (0) as a head of the signal frame (S303), if the value obtained by subtracting rc from tk is smaller than zero (0) (S301: yes).

Ec can be determined as a time which can be obtained by adding rc to tk (S305), if the value obtained by adding rc to tk is smaller than a last time (wn) of the signal frame (S304: no) and is also determined as wn as a tail end of the signal frame (S306), if the value obtained by adding rc to tk is larger than last time (wn) (S304: yes).

A process for leaving the speech information having a highest signal level can be carried out during a period from Bc to Ec. This will be described with reference to FIG. 7.

As shown in FIG. 7 (a), only the speech information pa having the maximum value is left and the other speech information should be abandoned although there are two or more speech information pa and pb having a higher signal level during the period from Bc to Ec. That is, as shown in FIG. 7 (b), it is only the signal "a" to be left during the period from Bc to Ec. A following mathematical expression (3) can be used to leave the maximum value (S307).

$$a_{c_k,t} = 0, \text{ for } t \in \left[B_c, t_k[\bigcup]t_k, E_c\right] \quad (3)$$

The in-channel stimulating frequency adjustment can be expressed by a following mathematical expression (4).

$$a_{m,n} = 0, \text{ where } |n - n_c| \leq \frac{1}{R_c}, n \in T \quad (4)$$

Then inter-channel stimulating frequency adjustment (S207) can be carried out such that the number of the stimulating pulses should be a frequency (impulse stimulating rate) allowed in the channel by leaving speech information having a high signal level in the signal frame.

Figure 8:
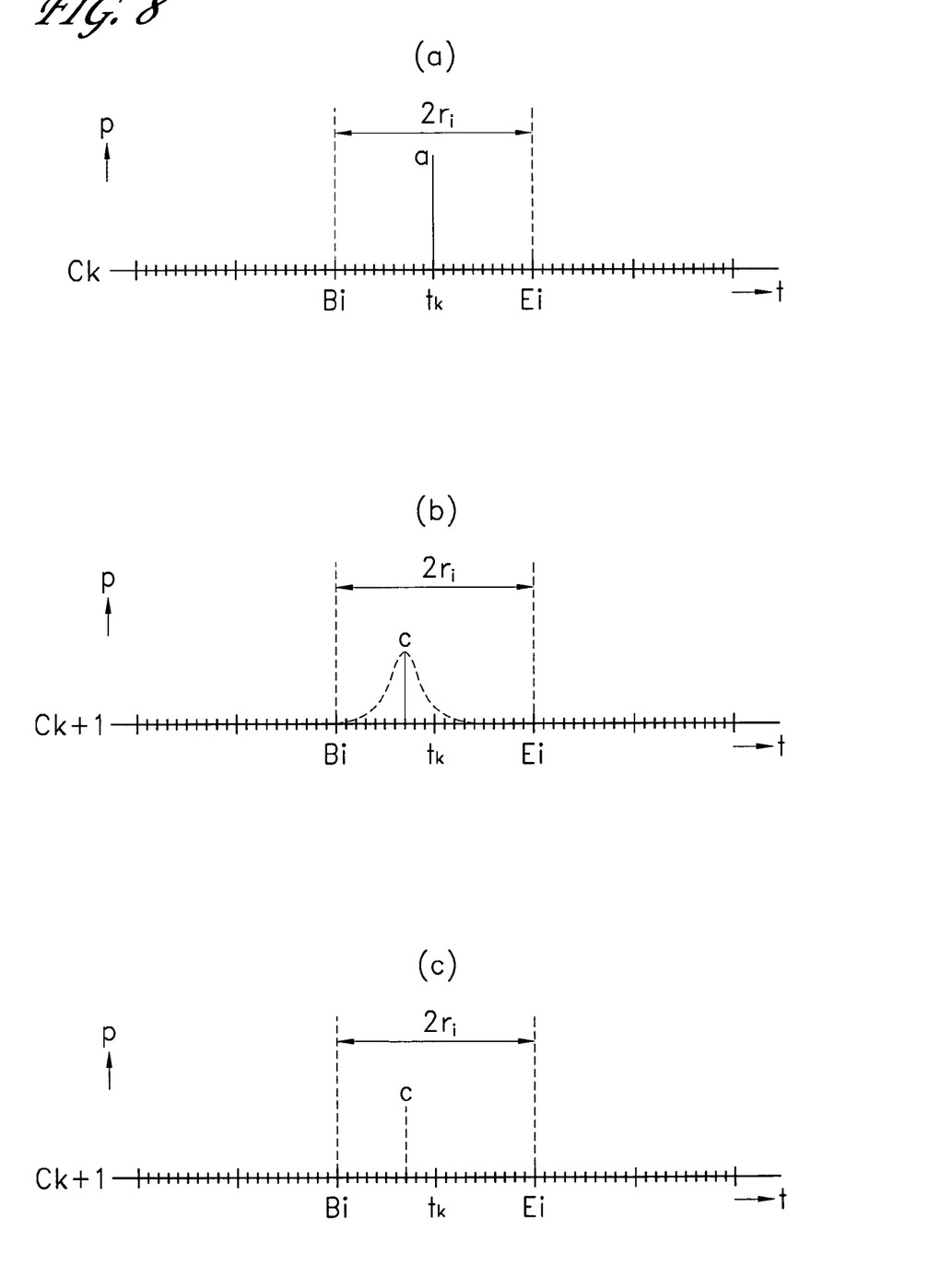
FIG. 8 includes timing diagrams of an operation of the inter-channel stimulating frequency adjusting module of the cochlear implant according to an embodiment.

The inter-channel stimulating frequency adjustment is described below with reference to FIG. 8. FIG. 8 (a) is a graph having the abscissa (time: t) and the ordinate (signal level: p) and shows a speech information after the in-channel stimulating frequency adjustment of the channel k(ck). The scale of the abscissa indicates the sampling rate. That is, the scale unit of the abscissa indicates the presence of the speech information before treatment. The sampling rate can be for example, but without limitation, 20 kHz.

A symbol "ri" can be the inverse number of the impulse stimulating rate Ri (e.g. 14400 pps) and indicates a period in which the presence of only one stimulating pulse is allowed. The impulse stimulating rate Ri can be a stimulating rate per one signal frame considering all channels.

Figure 5:
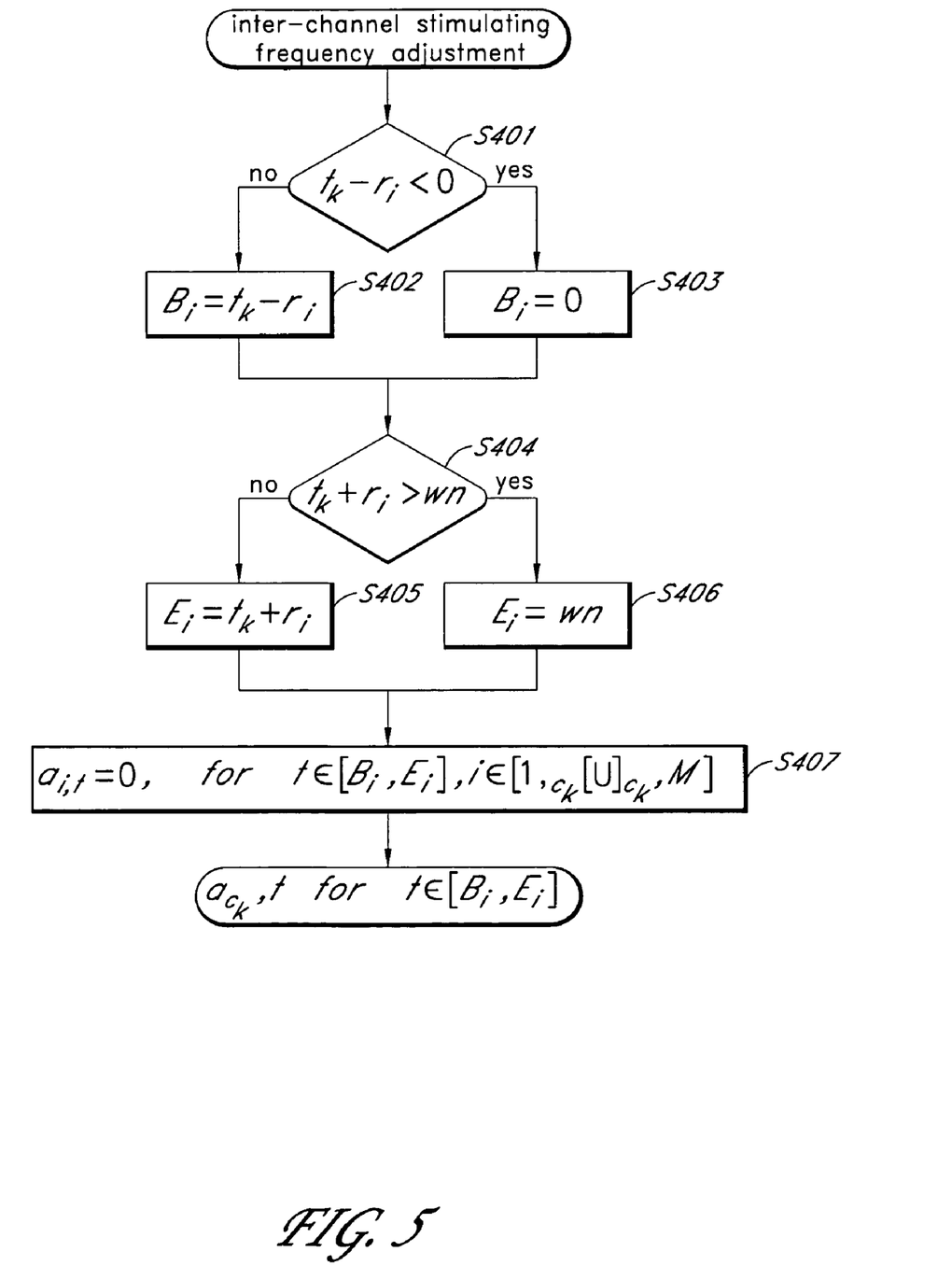
FIG. 5 is a flow chart showing an operation of the inter-channel stimulating frequency adjusting module of the cochlear implant according to an embodiment.

In one time inter-channel stimulating frequency adjustment, it should be processed during a period from a point of time (Bi) before from a point of time tk by a period ri, to a point of time (Ei) after from a point of time tk by a period ri. Bi can be determined as a time which can be obtained by subtracting ri from tk (S402), if the value obtained by subtracting ri from tk is larger than zero (0) (S401: no) and is also determined as zero (0) as a head of the signal frame (S403), if the value obtained by subtracting ri from tk is smaller than zero (0) (S401: yes).

Ei can be determined as a time which can be obtained by adding ri to tk (S405), if the value obtained by adding ri to tk is smaller than a last time (wn) of the signal frame (S404: no) and is also determined as (wn) as a tail end of the signal frame (S406), if the value obtained by adding ri to tk is larger than last time (wn) (S404: yes).

A process for leaving the speech information having a highest signal level can be carried out during a period from Bi to Ei. This process is described with reference to FIG. 8. As shown in FIGS. 8 (a) and 8 (b), when there is a signal "a" in a period from Bi to Ei at a channel ck and a signal "c" at a channel ck+1, only the signal "a" having a higher signal level is left and the other speech information should be abandoned. That is, as shown in FIG. 8 (c), it is only the signal "a" to be left during the period from Bi to Ei. A following mathematical expression (5) can be used to leave the maximum value (wherein $R_c < R_i$) (S407).

$$a_{i,t} = 0, \text{ for } t \in [B_i, E_i], i \in \left[1, c_k[\bigcup]c_k, M\right] \tag{5}$$

The inter-channel stimulating frequency adjustment can be expressed by a following mathematical expression (6).

$$a_{l,n} = 0, \text{ where } |n - n_i| \leq \frac{1}{R_i}, l \in I, n \in T \tag{6}$$

After this time, the processes (S202~S207) stated above can be repeated in one signal frame (S208). If the maximum value is zero (0) at a next period tk, no more process are required and thus the process can be completed (S203: yes). From these processes, the information tk of time can be put into signal level pk of sound information and the information ck of channel in respective counter k and can be output from the channel selection process (S104).

Figure 6:
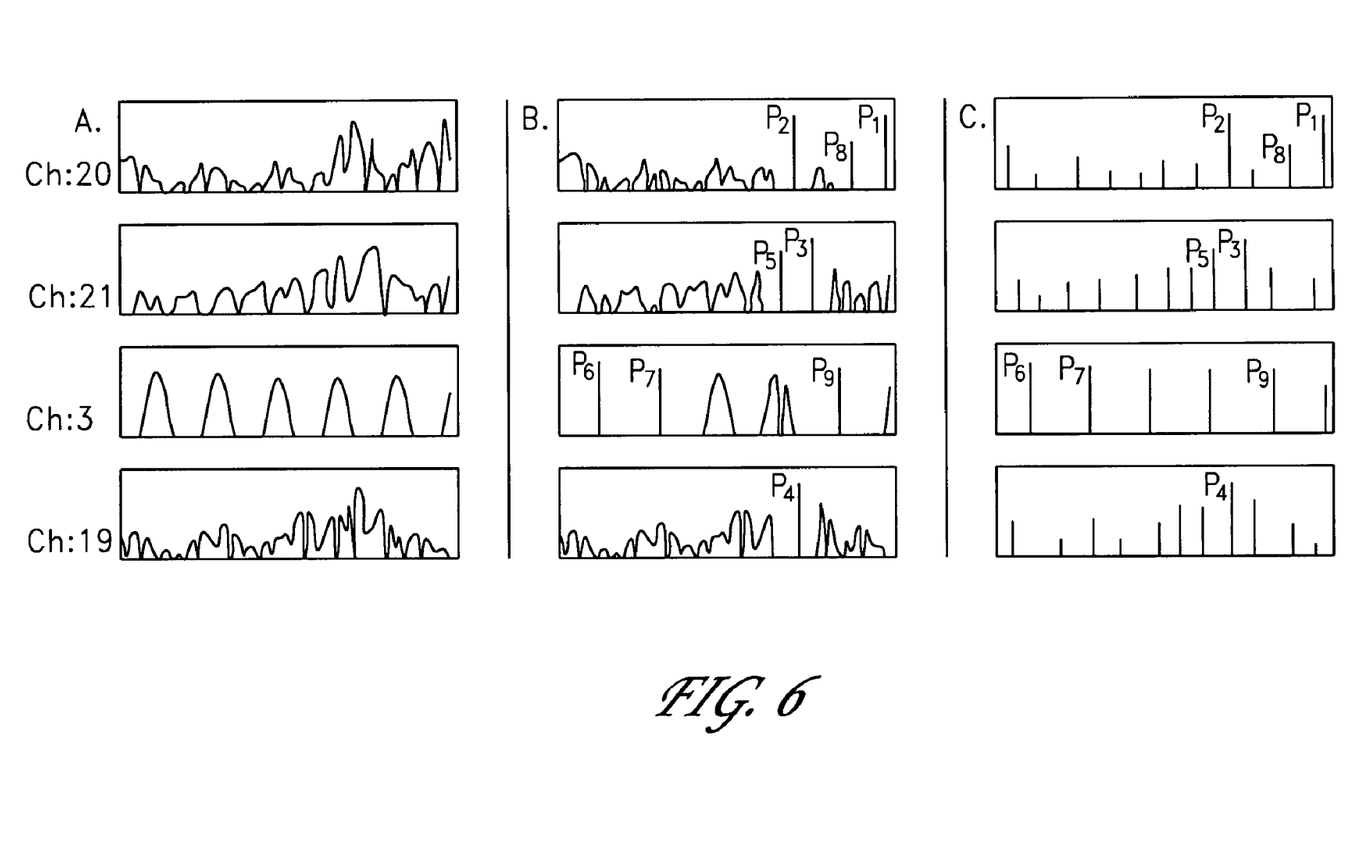
FIG. 6 is an explanatory view showing a channel selection process of the cochlear implant according to an embodiment.

The channel selection processes (S104) are shown in FIG. 6. FIG. 6A shows the sound information before processes of four (4) channels. As shown in FIG. 6B, a region near the signal p1 having a highest signal level in the signal frame can be firstly removed and then same process can be carried a signal p2 and thus same process can be carried out successively in the same channel. Such a process can be also carried out in other channels. Only sound information necessary for the stimulating pulses are finally left as shown in FIG. 6C.

Figure 9:
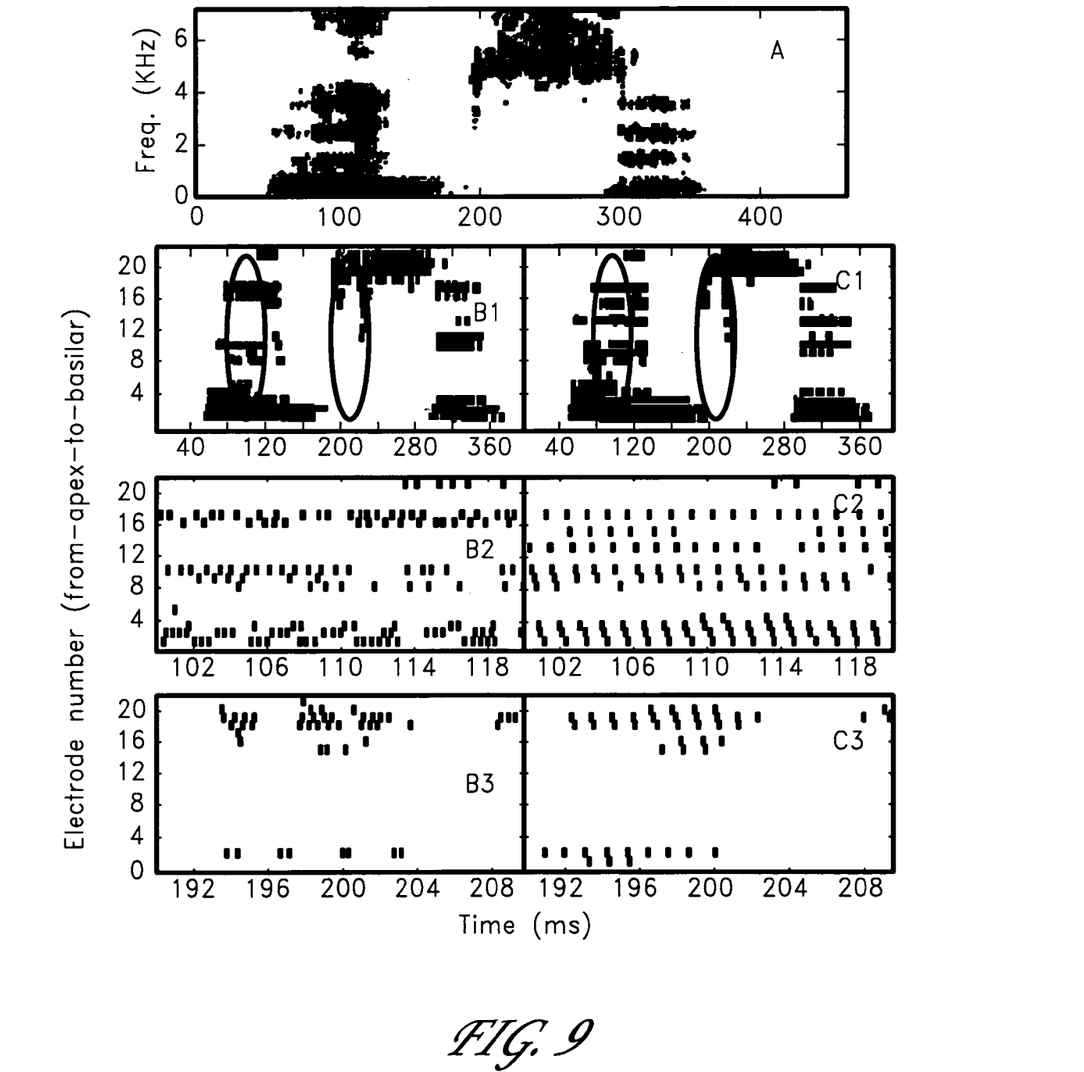
FIG. 9 is another explanatory view showing an operation of the cochlear implant according to an embodiment.

FIG. 9 shows results of an actual speech process in which human speech spoken as "utsu" can be processed. FIG. 9A is a spectrogram is this human speech before the process in which B1~B3 show outputs of results speech processed in accordance with an embodiment. On the other hand, C1~C3 show results processed by a conventional technology in comparison with the results of B1~B3. In B1~B3 (C1~C3), B1 (C1) shows a whole output of the signal frame and B2 (C2) is an enlargement of a front vertical ellipse and shows a portion "u" of the spoken speech "utsu". On the other hand, B3 (C3) is an enlargement of a central vertical ellipse and shows a portion "ts" of the speech "utsu".

Heretofore since it has been thought that it is preferable to output all sampled speech information as stimulations without omission in order to recreate the speech more faithfully to the actual speech, some of the simultaneously generated speech information have been output purposely later than other simultaneously generated speech information. However this delay results in an unnatural-sounding speech recreation. This unnatural condition is apparent from a fact that the outputs shown in C2 and C3 in FIG. 9 have become regular outputs. According to the present embodiments, the periodicity of the outputs of stimulation pulses in each channel can be obtained at a relatively high probability and it corresponds to the inverse number of the center frequency of corresponding channel.

The inventors of the present inventions have found that sufficiently comprehensible recreation of speech can be obtained by outputting only selected speech or sound information having a high signal level without outputting all sampled speech information as stimulations without omission. In addition, according to the speech processing method of the some of the present embodiments, it is possible to provide wearers of the cochlear implant 1 with speech that is more natural sounding speech since the relative time interval of the speech information to be regenerated can be better maintained.

Accordingly, in some embodiments of the cochlear implant 1, it is possible to regenerate natural variation of respective channels at a value near the natural period and at relatively high probability since only the speech information having the highest signal level within the period in which presence of only one stimulating pulse is allowed by in-channel and inter-channel stimulating frequency adjustments.

Although it is described with reference to a preferred embodiment that the adjustment of stimulation is carried out every one signal frame, it is also possible to carry out the stimulation adjustment in consideration of other signal frames.

In some embodiments, it is possible to provide wearers of the cochlear implant 1 with speech that is more natural-sounding since the same order as those of the generation of the speech information as well as the relative time interval of the speech information to be regenerated can be maintained because the speech information having high signal level being left in order to adjust the number of the stimulating pulses to be the allowed stimulation.

In some embodiments, it is possible to regenerate natural variation of respective channels at a value near the natural period and at relatively high probability since only the speech information having the highest signal level within the period in which presence of only one stimulating pulse is allowed.

In some embodiments, it is possible to provide wearers of the cochlear implant with speech that is more natural-sounding since the same order as those of the generation of the speech information as well as the relative time interval of the speech information to be regenerated can be maintained because the speech information having high signal level being left in order to adjust the number of the stimulating pulses to be the allowed stimulation.

In some embodiments, it is possible to regenerate natural variation of respective channels at a value near the natural period and at relatively high probability since only the speech information having the highest signal level within the period in which presence of only one stimulating pulse is allowed.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

What is claimed is:

1. A method of sound conversion in a cochlear implant in which an electrode array of a plurality of electrodes is arranged within a cochlea, each of the electrodes corresponding to one of a plurality channels, electrical stimulation pulses are generated by transmitting sound information sampled via a microphone to the electrodes, and the acoustic sense of the user is reinforced by transmitting the sound information to the cochlea as electrical stimulation pulses, the method comprises steps of:
   (1) discriminating the sound information into respective frequency bands using a plurality of band pass filters within a signal frame of a predetermined sampling period, to generate a sound information comprising a combination of channel information, time information and signal level information which is represented as an amplitude-time matrix(ATM), then;
   (2) successively repeating the following steps identified as (a) to (d);
   (a) adding to the sound information of ATM an information indicative of which channel corresponds to each frequency band;
   (b) determining a maximum value that is the highest signal level of each sound information of ATM, based on a magnitude of signal level of each sound information;
   (c) adjusting the number of the stimulation pulses to a frequency allowed in each channel in relation to said maximum value by leaving, within a time interval within each channel, only a sound information having the highest signal level in each channel, so that the other sound information within the time interval within each respective channel is abandoned; then
   (d) adjusting the number of the stimulation pulses to a frequency allowed in all channels by leaving, for a given time interval for all channels, only a sound information having the highest signal level of the sound information left in said all channels, so that the other sound information in said all channels is abandoned; and
   generating the stimulation pulses by providing the remaining sound information having the combination of ATM to the electrodes corresponding to the respective channels.

2. A method according to claim 1 in which only one sound information having a highest signal level is left if there are a plurality of sound information within a period in which presence of only one stimulation pulse in one channel is allowed when adjusting the frequency of the stimulation pulses in respective channels.

3. A method according to claim 1 in which only one sound information having a highest signal level is left if there are a plurality of sound information within a period in which presence of only one stimulation pulse in one channel is allowed when adjusting the frequency of the stimulation pulses in all channels.

4. A cochlear implant comprising an electrode array of a plurality of electrodes configured to be arranged within a cochlea, each of the plurality of electrodes corresponding to one of a plurality channels, an electrical stimulation pulse module configured to generate electrical stimulation pulses corresponding to sound sampled via a microphone and to transmit the pulses to the electrodes, whereby the acoustic sense of a user is reinforced by transmitting the sound information to the cochlea as electrical stimulation pulses, the cochlear implant further comprising:

a channel information adding means for adding an information of each channel corresponding to each frequency band, to the sound information after discriminating the sound information into respective frequency bands using a plurality of band pass filters within a signal frame of a predetermined sampling period, to generate a sound information comprising a combination of channel information, time information and signal level information, represented as an amplitude-time matrix (ATM);
   an in-channel stimulation frequency adjusting means for adjusting the number of the stimulation pulses to a frequency allowed in each channel in relation to said maximum value by leaving within a time interval within each channel, only a sound information having a highest signal level, so that the other sound information within the time interval within each respective channel is abandoned;
   an inter-channel stimulation frequency adjusting means for adjusting the number of the stimulation pulses to a frequency allowed in all channels by leaving, for a given time interval for all channels, only a sound information having the highest signal level of the sound information left in all channels, so that the other sound information in said all channels is abandoned; and
   a stimulation pulse generating means for converting the remaining sound information having the combination of ATM to the stimulation pulse and providing the stimulation pulse to the electrodes corresponding to the respective channels.

5. A cochlear implant according to claim 4 in which the in-channel stimulation frequency adjusting means leaves only one sound information having a highest signal level if there are a plurality of sound information within a period in which presence of only one stimulation pulse in one channel is allowed.

6. A cochlear implant according to claim 4 in which the inter-channel stimulation frequency adjusting means leaves only one sound information having a highest signal level if there are a plurality of sound information within a period in which presence of only one stimulation pulse between channels is allowed.

7. A cochlear implant comprising an electrode array of a plurality of electrodes configured to be arranged within a cochlea, each of the electrodes corresponding to one of a plurality channels, electrical stimulation pulse module configured to generate electrical stimulation pulses corresponding to sound sampled via a microphone and to transmit the pulses to the electrodes, whereby the acoustic sense of a user is reinforced by transmitting the sound information to the cochlea as electrical stimulation pulses, the cochlear implant further comprising:
   a channel information adding module configured to correlate the sound information into respective frequency bands using a plurality of band pass filters within a signal frame of a predetermined sampling period and to add an information of a channel corresponding to the frequency band to the sound information to generate a sound information comprising a combination of channel information, time information and signal level information, represented as an amplitude-time matrix (ATM);
   an in-channel stimulation frequency adjusting module configured to limit the number of the stimulation pulses to a frequency allowed in each channel, in relation to said maximum value by leaving, within a time interval within each channel, only a sound information having a highest signal level, so that the other sound information within the time interval within each channel is abandoned;

an inter-channel stimulation frequency adjusting module configured to limit the number of the stimulation pulses to a frequency allowed in all the channels by leaving, for a given time interval for all channels, only a sound information having the highest signal level of the sound information left in all channels, so that the other sound information in said all channels is abandoned; and a stimulation pulse generating module configured to convert the remaining sound information having the combination of ATM into stimulation pulses and providing the stimulation pulses to the electrodes corresponding to the respective channels.

* * * * *

UNITED STATES PATENT AND TRADEMARK OFFICE
CERTIFICATE OF CORRECTION

PATENT NO. : 7,627,379 B2
APPLICATION NO. : 11/349423
DATED : December 1, 2009
INVENTOR(S) : Kitazawa et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 771 days.

Signed and Sealed this

Second Day of November, 2010

David J. Kappos
*Director of the United States Patent and Trademark Office*